United States Patent [19]

Kowalski

[11] Patent Number: 5,305,090
[45] Date of Patent: Apr. 19, 1994

[54] BIREFRINGENT INSPECTION POLARSCOPE

[75] Inventor: Henry C. Kowalski, Grand Blanc, Mich.

[73] Assignee: GMI Engineering and Management Institute, Flint, Mich.

[21] Appl. No.: 805,079

[22] Filed: Dec. 11, 1991

[51] Int. Cl.$^5$ .................................................. G01J 4/00
[52] U.S. Cl. ........................................ 356/366; 356/365
[58] Field of Search ........................... 356/364–370, 356/446, 32, 33, 34, 35; 250/225; 359/494

[56] References Cited

U.S. PATENT DOCUMENTS

| | | | |
|---|---|---|---|
| H76 | 7/1986 | Cotterman | 356/366 |
| 2,332,308 | 10/1943 | Dresser . | |
| 3,031,919 | 5/1962 | Collyer | 88/14 |
| 3,177,761 | 4/1965 | Redner | 88/14 |
| 3,373,652 | 3/1968 | Flader | 356/33 |
| 3,466,129 | 9/1969 | Agatsuma et al. | 356/365 |
| 3,495,910 | 2/1970 | Kuroha et al. | 356/115 |
| 3,549,259 | 12/1970 | Kzatchko | 356/366 |
| 3,653,767 | 4/1972 | Liskowitz | 356/366 |
| 3,687,555 | 8/1972 | Yamamoto et al. | 356/365 |
| 3,741,660 | 6/1973 | Abu-Shumays et al. | 356/364 |
| 3,811,775 | 5/1974 | Abu-Saud | 356/365 |
| 3,819,948 | 6/1974 | Iijima et al. | 356/364 |
| 3,873,207 | 3/1975 | Bryngdahl | 356/366 |
| 3,885,875 | 5/1975 | Rosenfeld et al. | 356/369 |
| 4,171,908 | 10/1979 | Robert et al. | 356/366 |
| 4,297,032 | 10/1981 | Temple | 356/366 |
| 4,309,110 | 1/1982 | Tumerman | 356/366 |
| 4,332,474 | 6/1982 | Miller | 356/366 |
| 4,400,062 | 8/1983 | Mori et al. | 356/365 |
| 4,410,277 | 10/1983 | Yamamoto et al. | 356/369 |
| 4,547,067 | 10/1985 | Watanabe | 356/239 |
| 4,684,256 | 8/1987 | Tsumura et al. | 356/367 |
| 4,786,802 | 11/1988 | Yoshii et al. | 356/366 |
| 4,810,089 | 3/1989 | Murakoshi et al. | 356/367 |

Primary Examiner—Richard A. Rosenberger
Assistant Examiner—Hoa Q. Pham
Attorney, Agent, or Firm—Brooks & Kushman

[57] ABSTRACT

A birefringent inspection polariscope for inspecting relatively transparent objects for defects is disclosed as having a source of white light to emit light along a path and, positioned in the path, a retarder to diffuse light from the source thereof, a fixed polarizer to circularly polarize the light and a fixed, circularly polarizing analyzer to convert circularly polarized light emanating from the polarizer to plane polarized light. An inspection area, in which to position an object to be inspected, is provided between the polarizer and the analyzer; and a lens is positioned to magnify light emanating from the analyzer. Also provided is a half-wave plate that can be positioned in the path of light to provide a dark background field to facilitate photographic recording.

12 Claims, 2 Drawing Sheets

BIREFRINGENT INSPECTION POLARSCOPE

TECHNICAL FIELD

This invention relates to birefringent inspection polariscopes having circularly polarizing polarizer and analyzer plates that are fixed.

BACKGROUND ART

Polariscopes for inspecting relatively transparent objects for defects are well known in the art. For example, U.S. Pat. No. 3,177,761 to Redner discloses a polariscope having simultaneously rotatable waveplates to permit measurement of the relative retardation and azimuth of a specimen without having to remove or replace any of the polarizing elements.

U.S. Pat. No. 3,687,555 to Yamamoto et al. discloses a photoelectric polarization analyzer that introduces a half-wave polarizer plate that is rotated in place of elements of the polarization system.

U.S. Pat. No. 3,434,786 to Flynn et al. discloses a dual-beam polariscope using condenser lenses, polarizers and mirrors to obtain two images of a specimen that are focused by a single lens adjustment.

U.S. Pat. No. 3,811,775 to Abu-Saud discloses a stress determining polariscope using plane polarized, polychromatic light that can be swept back and forth across a transparent object being inspected. The object can also be moved along an axis that is transverse to that along which the light is being swept.

U.S. Pat. No. 4,547,067 to Watanabe discloses a fault polariscope for detecting faults and foreign matter in transparent objects. Diffused light transmitted through an object is imaged through a lens system and converted into an electrical signal by a photoelectric detector and processed.

Other patents that are representative of polariscope systems include U.S. Pat. No's. 2,332,308; 3,031,919; 3,373,652; 3,466,129; 3,495,910; 3,549,259; 3,653,767; 3,873,207; 4,171,908; 4,297,032; 4,309,110; 4,400,062; 4,410,277; 4,684,256; and 4,786,802. Also representative is U.S. Statutory Invention Registration No. H76.

While each of these polariscopes functions with a certain degree of efficiency, none discloses the advantages of the improved polariscope of the present invention as is hereinafter more fully described.

DISCLOSURE OF INVENTION

An object of the present invention is to provide an improved polariscope the elements of which are fixed and require no physical adjustment during the use of the polariscope.

Another object of the present invention is to provide a polariscope having the capability of darkening the background of a field of view to facilitate photographing light patterns produced by polarized light passing through a specimen being examined.

Yet another object of the present invention is to provide a polariscope having an emergent light intensity that is independent of the direction of the principal indices of a specimen being examined.

Still another object of the present invention is to provide a polariscope capable of magnifying light emerging from an analyzer thereof.

Another object of the present invention is to provide a polariscope capable of being used to examine an elongate or relatively continuous specimen and also a number of discrete specimens.

Yet another object of the present invention is to provide a polariscope elements of which can be oriented to maximize the comfort and convenience of an operator using the polariscope while standing or sitting at various elevations with respect to the polariscope.

Still another object of the present invention is to provide a polariscope that is relatively inexpensive to manufacture and maintain.

In realizing the aforementioned and other objects, the polariscope of the present invention includes a support member upon which the elements of the polariscope are mounted. A source of white light is mounted on the support and disposed to emit light along a path. A retarder is mounted on the support in the path of the light to diffuse light emitted from the source of white light, and a first circular polarizer is mounted on the support for receiving and circularly polarizing light emanating from the retarder.

A second circular polarizer is mounted on the support for receiving and plane polarizing circularly polarized light emanating from the first circular polarizer. An examination area is defined in the path of light between the first and second circular polarizers, proximate the first circular polarizer, for receiving a specimen, or object, to be examined.

If the object to be examined is homogeneous, it will have relatively uniform birefringent characteristics; and emergent light will appear to be a specific color. Imperfections in the specimen will have different birefringent characteristics, and light emerging therefrom will appear to be a different color.

A magnifying lens is mounted on the support for magnifying images formed by light emanating from the second circular polarizer. An additional half-wave polarizer is disposed between the first and second polarizers. It is pivotally mounted on the support and is pivotable to a first position, wherein the half-wave polarizer does not intercept the path of light, and to a second position, wherein the half-wave polarizer does intercept the path of light. When the half-wave polarizer is positioned in the path of light, the background surrounding an image formed by light emanating from the second circular polarizer is darkened to facilitate photographically recording the image.

The support includes a base, a housing, a polarizer frame, a support post, and an analyzer frame. The source of white light includes at least one fluorescent lamp and is mounted to, and is at least partially contained within, the housing. A reflector is mounted within the housing adjacent the lamp to direct light emitted thereby along the path of light.

The polarizer frame is mounted to the housing and at least partially contains the retarder and the first circular polarizer therein. The retarder and first circular polarizer are disposed so that the path of light respectively passes sequentially therethrough.

The support post has an upper end and a lower end. Its lower end is mounted to the housing, and its upper end extends generally upwardly away from the housing. The support post is disposed substantially parallel to the path of light. Mounted to the upper end of the support post is the analyzer frame, which at least partially contains the second circular polarizer and the magnifying lens. The second circular polarizer and the magnifying lens are disposed so that the path of light respectively passes sequentially therethrough. The half-wave polarizer is pivotally mounted to the support post between the first and second circular polarizers and proximate the second circular polarizer.

The housing is rotatably mounted to the base. The housing has an axis about which it has limited freedom to rotate. Since the polarizer frame, the support post and the analyzer frame are all directly or indirectly attached to the housing, these elements revolve about the axis whenever the housing is rotated thereabout. Accordingly, the path of light is angularly displaced about the axis by an equal amount.

The objects, features and advantages of the present invention are readily apparent from the following detailed description of the best mode for carrying out the invention when taken in connection with accompanying drawings.

BRIEF DESCRIPTION OF DRAWINGS

A more complete appreciation of the invention and many of the attendant advantages thereof may be readily obtained by reference to the following detailed description when considered with the accompanying drawings, in which like reference characters indicate corresponding parts in all the views, wherein.

BEST MODE FOR CARRYING OUT THE INVENTION

Figure 1:
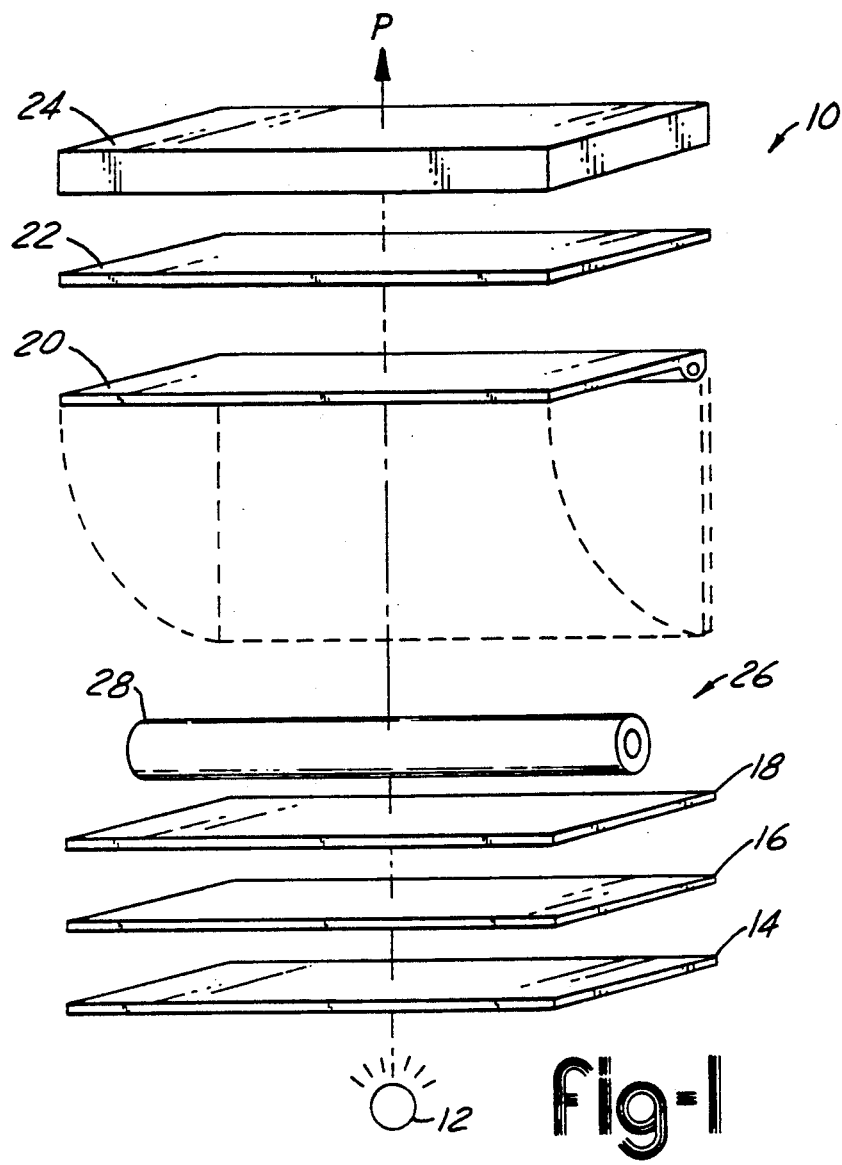
FIG. 1 is a simplified, exploded view of the major elements of the present invention.

A representation of the major elements of the preferred embodiment of the polariscope, generally indicated by the reference numeral 10, of the present invention is shown in FIG. 1 of the drawings. The elements are shown in their sequential positions relative to one another. The elements are mounted on a support; but, for the sake of simplicity, the support is not shown in this figure. A source of white light 12 is oriented to emit light along a path P. A light diffuser 14, a first circular polarizer 16, a first circular polarizer glass cover plate 18, a half-wave polarizer 20, a second circular polarizer, or analyzer 22, and a magnifying lens 24 are disposed so that the path P of light respectfully passes sequentially therethrough.

An inspection area, generally indicated by the reference numeral 26, is provided adjacent the side of the first circular polarizer glass cover plate 18 opposite from the source of white light 12. A representative object 28 is shown disposed in the inspection area 26 and in the path P of light. Inspections can be performed with equal facility on elongate objects passed continuously through the inspection area and on individually inserted discrete objects.

Light from the source of light 12 is diffused as it passes through the light diffuser 14 and is circularly polarized as it passes through the first circular polarizer 16. The emergent light from the second circular polarizer, or analyzer 22, is plane polarized. Intermediate the first circular polarizer 16 and the analyzer 22, light passes through the object 28 to be inspected. If the object 28, for example, a medical catheter, to be examined is homogeneous, it will have relatively uniform birefringent characteristics; and emergent light will appear to be a specific color. Imperfections in the object 28, however, will have different birefringent characteristics, and light emerging from the object 28 after passing through an imperfection will appear to be a different color.

It should be noted that no physical adjustment of the first circular polarizer 16 or of the second circular polarizer, or analyzer 22, are required. Indeed, as is described herein, these elements are fixedly mounted. Since these elements are circular polarizers, emerging light intensity is independent of the direction of principal stresses.

Figure 2:
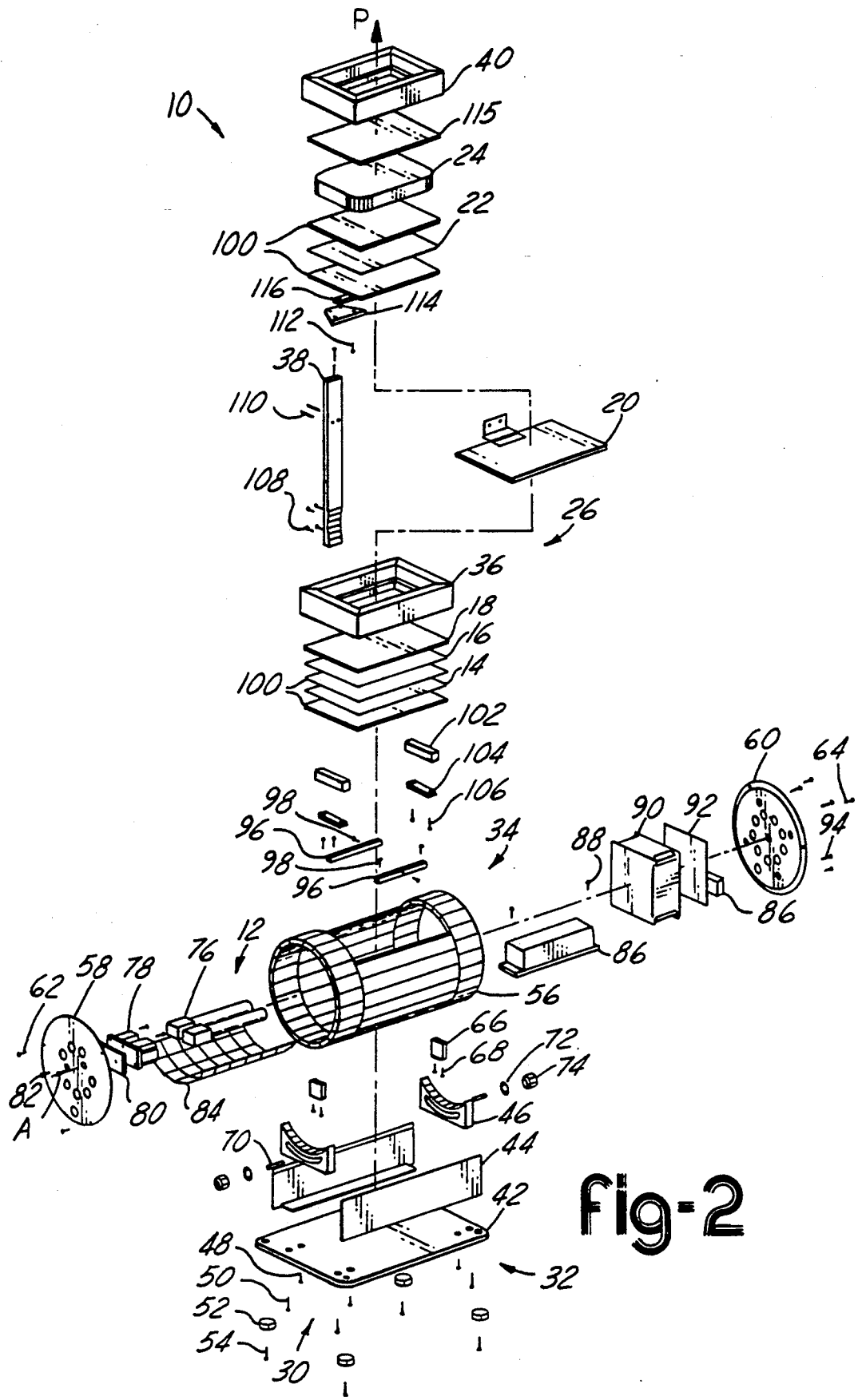
FIG. 2 is an exploded view of a preferred embodiment of the present invention.

FIG. 2 of the drawings shows a detailed, exploded view of a preferred embodiment of the polariscope, generally indicated by the reference numeral 10, of the present invention. A support, generally indicated by the reference numeral 30, includes a base, generally indicated by the reference numeral 32, a housing, generally indicated by the reference numeral 34, a polarizer frame 36, a support post 38, and an analyzer frame 40.

The base 32 includes a horizontally disposed base plate 42, a pair of cover plates 44, and a pair of housing cylinder mounts 46. The base plate 42 is rectangular, having two opposite edges of major dimension and two opposite edges of minor dimension. Secured along each of the edges of major dimension is a cover plate 44, the cover plates 44 being secured to the base plate 42 with cover plate screws 48. Secured along each of the edges of minor dimension is a housing cylinder mount 46, the latter being secured to the base plate 42 with cylinder mount screws 50. A rubber foot 52 is mounted to the underside of the base plate 42 proximate each corner thereof with a rubber foot screw 54.

The housing 34 includes a housing cylinder 56, a first end cap 58, and a second end cap 60. The housing cylinder 56 has a longitudinal axis A. The first end cap 58 is secured to the housing cylinder 56 with first end cap screws 62, and the second end cap 60 is secured to the housing cylinder 56 with second end cap screws 64. The housing cylinder 56 is supported proximate each end by a housing cylinder mount 46, each of which defines therein an arcuate slot having a radius extending from the axis A.

An adjustment bracket 66 is attached, with adjustment bracket screws 68, to the outside of the housing cylinder 56 proximate each end thereof. The adjustment brackets 66 extend downwardly between the housing cylinder mounts 46. A threaded stud 70 is secured to each adjustment bracket 66 and extends through the arcuate slot in each housing cylinder Mount 46. A washer 72 is disposed on each threaded stud 70, and a knurled thumbnut 74 is threaded thereupon.

With the thumbnuts 74 loosely fitted, the housing 34 can be rotated about the axis A over an angular displacement equal to that of the arcuate slot in each housing cylinder mount 46. With the thumbnuts 74 tightly secured, each adjustment bracket 66 attached to the housing cylinder 56 is pulled against an associated housing cylinder mount 46 attached to the base plate 42; and the housing cylinder 56 is prevented from being rotated with respect thereto.

Since the polarizer frame 36, the support post 38 and the analyzer frame 40 are all directly or indirectly attached to the housing cylinder 56, these elements revolve about axis A whenever the housing cylinder 56 is rotated thereabout. Accordingly, the path P of light is angularly displaced about axis A by an equal amount. This feature enables a tester using the polarizer 10 to examine objects to adjust the angle of viewing to accommodate a standing viewing position, looking directly downwardly into the magnifying lens 24, or a sitting position, looking into the magnifying lens 24 at an acute angle with respect to the horizontal. Such adjustments equally facilitate the examination of continuous, elongate objects and of small, discrete objects.

The source of white light 12 includes at least one fluorescent lamp 76 such as an Osram Dulux S 13W USA F13TT/50K light bulb obtained from Candela's Corporation, Santa Ana, Calif. The electric lamp 76 is supported by a lamp holder 78 affixed to a lamp holder mounting plate 80 secured to the first end cap So with mounting plate screws 82. A reflector 84 is disposed within the housing 34 adjacent the fluorescent lamp 76 to direct light emitted thereby along the path P of light. A lamp ballast 86 is secured within the housing cylinder 56 with lamp ballast screws 88.

A fan 90 and a fan filter 92 are secured to the second end cap 60 with fan screws 94. An electrical switch 87 is also secured to the second end plate 60. The electrical switch 87 controls the application of electrical energy to the fluorescent lamp 76 and to the fan 90.

The housing cylinder 56 defines a rectangular opening therein having two opposite edges extending parallel to the axis A. Disposed along each of the edges is a polarizer frame holder 96 secured thereto with polarizer frame holder screws 98. The polarizer frame 36 is secured to the polarizer frame holder 96 with polarizer frame holder screws 98.

Secured within the polarizer frame 36 are the light diffuser 14, the first circular polarizer 16, and the first circular polarizer glass cover plate 18. The circular polarizer 16 is constructed of circular Polaroid HNCP37, and it and the diffuser and retarder were obtained from the Polaroid Polarizer Division, Norwood, Mass. The light diffuser 14 is also sandwiched between two additional glass plates 100. The light diffuser 14, the first circular polarizer 16, and the first circular polarizer glass cover plate 18 are mounted within the polarizer frame 36 by a pair of glass clamps 102. The glass clamps 102 are held in place by glass clamp holders 104 secured to the polarizer frame 36 by glass clamp holder screws 106.

The support post 38 has an upper end and a lower end, its lower end being secured to the housing cylinder 56 with support post screws 108. The half-wave polarizer 20 is pivotally secured to the support post by half-wave polarizer screws 110. The half-wave polarizer 20 is pivotable to a first position, shown in phantom lines and wherein it does not intercept the path P of light, and to a second position, wherein it does intercept the path P of light. When the half-wave polarizer 20 is positioned in the path P of light, the background surrounding an image formed by light emanating from the analyzer 22 is darkened to facilitate photographically recording the image.

The analyzer frame 40 is secured, with polarizer frame mounting plate screws 112, to a polarizer frame mounting plate 114, which in turn is secured to the support post 38 with similar screws 112. Secured within the analyzer frame 40 are the second circular polarizer, or analyzer 22, and the magnifying lens 24. A magnifying lens glass cover plate 115 is disposed adjacent the opposite side of the magnifying lens from the second circular polarizer 22. The second circular polarizer 22 is sandwiched between additional plates of glass 100. The analyzer 22, the magnifying lens 24 and the additional plates of glass are held in place within the analyzer frame 40 by an analyzer frame plate holder 116. In the preferred embodiment, a magnifying lens 24 having a magnification within a range of 2 to 3 diameters, and preferably of approximately 2.5 diameters, is used; a magnification of 2.5 diameters indicating that the magnifying lens 24 is capable of forming an image the size of which is 2.5 times the actual size of an associated object viewed through the lens.

Figure 3:
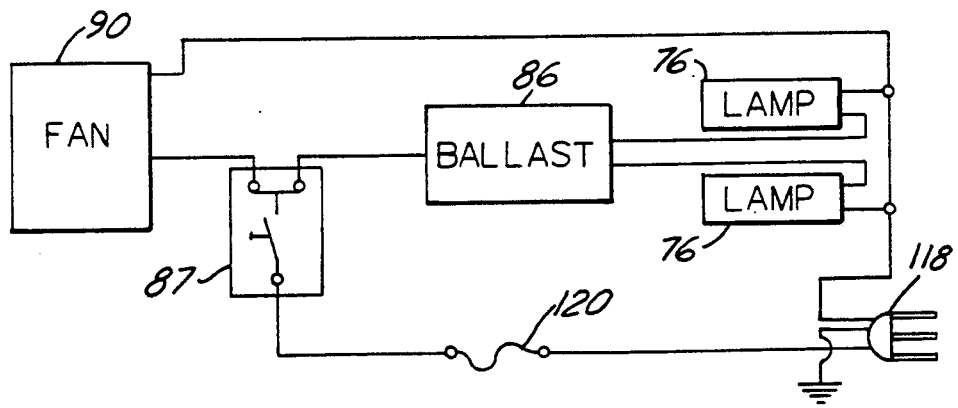
FIG. 3 is a schematic view of an electrical circuit for manually controlling light and cooling elements of the present invention.

FIG. 3 of the drawings is a schematic diagram of an electrical circuit for manually controlling light and cooling elements of the present invention. Elements of the circuit shown include an electrical connector 118, a fuse 120, and the switch 87. Connected in series with the switch 87 is the fan 90. Also connected in series with the switch 87, and in parallel across the fan 90, is a lamp ballast 86 feeding two parallel lamps 76. When contacts of the switch 87 are closed, the fan 90 and the lamps 76 are supplied with electrical energy. When contacts of the switch 87 are open, electrical energy is removed therefrom.

While the best mode for carrying out the invention has been described in detail, those familiar with the art to which this invention relates will recognize various alternative designs and embodiments for practicing the invention as disclosed by the following claims.

What is claimed is:

1. A polariscope for inspecting relatively transparent objects for defects, the polariscope comprising:
   a base;
   a housing mounted on the base;
   a polarizer frame mounted on the housing;
   a support post having an upper and a lower end, the lower end being mounted on the housing, the upper end extending generally upwardly away from the housing;
   an analyzer frame mounted to the upper end of the support post;
   a source of white light mounted at least partially within the housing and disposed to emit light along a path generally parallel to the support post;
   a first circular polarizer fixedly mounted at least partially within the polarizer frame for receiving and circularly polarizing light emanating from the source of white light;
   a second circular polarizer fixedly mounted at least partially within the analyzer frame for receiving circularly polarized light emanating from the first circular polarizer, an examination area being defined in the path of light between the first and second circular polarizers, proximate the first circular polarizer, for receiving an object to be examined;
   a half-wave polarizer mounted on the support in the path of light between the first and second polarizers, the half-wave polarizer being displaceable between a first position, wherein the half-wave polarizer does not intercept the path of light, and a second position, wherein the half-wave polarizer intercepts the path of light, thereby darkening the background surrounding an image formed by light emanating from the second circular polarizer; and
   a magnifying lens mounted at least partially within the analyzer frame for magnifying images formed by light emanating from the second circular polarizer.

2. The polariscope as defined by claim 1, wherein the source of white light is a fluorescent lamp.

3. The polariscope as defined by claim 1, wherein the magnifying lens has a magnification such that the lens is capable of forming an image the size of which is within a range extending between and including two and three times the actual size of an associated object viewed through the lens.

4. The polariscope as defined by claim 1, further including a diffuser mounted at least partially within the polarizer frame in the path of light for diffusing light emitted from the source of white light.

5. The polariscope as defined by claim 1, wherein the half-wave polarizer is pivotally mounted on the support and is pivotable between a first position, wherein the half-wave polarizer does not intercept the path of light, and a second position, wherein the half-wave polarizer intercepts the path of light.

6. The polariscope as defined by claim 1, wherein the housing is rotatably mounted to the base, the housing having an axis about which it has limited freedom to rotate, the polarizer frame respectively revolving about the axis whenever the housing is rotated thereabout, the path of white light being angularly displaced about the axis by an equal amount.

7. The polariscope as defined by claim 6, further including a first circular polarizer glass cover plate disposed between the first circular polarizer and the examination area.

8. The polariscope as defined by claim 7, further including a magnifying lens glass cover plate disposed adjacent the side of the magnifying lens opposite from the second circular polarizer.

9. The polariscope as defined by claim 8, further including a first glass plate disposed adjacent the side of the light diffuser opposite from the first circular polarizer.

10. The polariscope as defined by claim 9, further including a second glass plate disposed between the light diffuser and the first circular polarizer.

11. The polariscope as defined by claim 10, further including a third glass plate disposed adjacent the side of the second circular polarizer opposite from the magnifying lens.

12. The polariscope as defined by claim 11, further including a fourth glass plate disposed between the second circular polarizer and the magnifying lens.

* * * * *